United States Patent
Viertl

(10) Patent No.: US 6,952,094 B1
(45) Date of Patent: Oct. 4, 2005

(54) NONDESTRUCTIVE INSPECTION METHOD AND SYSTEM THEREFOR

(75) Inventor: John Ruediger Mader Viertl, Niskayuna, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 10/905,258

(22) Filed: Dec. 22, 2004

(51) Int. Cl.⁷ .................. G01N 27/82; G01N 27/90
(52) U.S. Cl. ........................... 324/238; 324/220
(58) Field of Search .................. 324/219–221, 324/238–241, 234, 260–262; 73/866.5

(56) References Cited

U.S. PATENT DOCUMENTS

| | | | |
|---|---|---|---|
| 4,706,020 A | 11/1987 | Viertl et al. | 324/238 |
| 6,426,622 B1 | 7/2002 | Givens et al. | 324/262 |
| 6,477,773 B1 | 11/2002 | Wilson et al. | 29/889.1 |
| 6,545,467 B1 | 4/2003 | Batzinger et al. | 324/219 |
| 6,608,478 B1 | 8/2003 | Dziech et al. | 324/262 |

Primary Examiner—Bot LeDynh
(74) Attorney, Agent, or Firm—Ernest Cusick; Gary M. Hartman; Domenica N. S. Hartman

(57) ABSTRACT

A method and system for inspecting a turbine wheel having axial slots along a perimeter thereof that are configured for mating with and securing airfoil members to the perimeter of the wheel, and an annular slot that intersects the axial slots. The method and system make use of one or more eddy current probes that are placed in the annular slot to electromagnetically inspect the annular slot and at least one of the axial slots for cracks in surfaces thereof. The probe is part of a probe assembly that includes a mounting member for engaging at least one of the annular and axial slots. The probe assembly is operable to maintain the probe at a fixed distance from surfaces of the annular slot as the probe travels through the annular slot.

20 Claims, 3 Drawing Sheets

NONDESTRUCTIVE INSPECTION METHOD AND SYSTEM THEREFOR

BACKGROUND OF THE INVENTION

The present invention generally relates to nondestructive inspection methods and systems. More particularly, this invention relates to a method and system for scanning a turbine wheel with an eddy current probe, and particularly surface regions of slots within the wheel.

Various nondestructive examination (NDE) techniques have been used to perform nondestructive testing on articles. An example is eddy current probe inspection of turbine components, as disclosed in commonly-assigned U.S. Pat. Nos. 4,706,020, 6,426,622, and 6,545,467, whose disclosures pertaining to the construction, operation, and use of eddy current probes are incorporated herein by reference. A component of particular interest is industrial gas turbine wheels to which the buckets of the turbine are mounted. In the hostile operating environments of gas turbines, the structural integrity of the turbine wheels within its turbine section is of great importance in view of the high mechanical stresses that wheels must be able to continuously withstand at high temperatures. The regions of a wheel forming the slots into which the buckets are secured, typically in the form of what are known as dovetail slots, are known to eventually form cracks over time, necessitating monitoring of the wheel in these regions. In some wheel designs, such as the stages 1, 2, and 3 wheels of the General Electric 7FA gas turbine, cooling of the buckets and wheel perimeter is assisted by the presence of a cooling slot located near the perimeter of the wheel and into which the dovetail slots extend. Over extended periods of time under the severe operating conditions of a wheel, cracks may form at common edges formed where the dovetail slots and cooling slot intersect. The ability to detect cracks with lengths of as little as 60 mils (about 1.5 mm) and even less is desirable in order to provide sufficiently early detection to avoid catastrophic failure of turbine wheels.

While a turbine rotor can be completely disassembled to gain access to its individual wheels, inspection techniques that can be performed with limited disassembly are preferred to minimize downtime, such as to fit within outage schedules of a gas turbine employed in the power generating industry. Since buckets are typically removed for inspection, it would be preferred if the dovetail and cooling slots of a turbine wheel could be examined with only the buckets removed. However, access to the cooling slot is very limited, and any inspection technique using an eddy current probe must address the difficulty of bringing the probe into stable, near-proximity to the surfaces being tested.

BRIEF SUMMARY OF THE INVENTION

The present invention provides a method and system for inspecting a turbine wheels having axial slots along a perimeter thereof that are configured for mating with and securing airfoil members to the perimeter of the wheel, and an annular slot that intersects the axial slots. The method and system make use of at least one eddy current probe that is sized and configured to be placed in the annular slot to electromagnetically inspect the annular slot and the axial slots for cracks in surfaces thereof.

The inspection system of this invention generally includes a probe assembly having an eddy current probe that is sized and configured to be received in the annular slot. The probe assembly further includes a mounting member having means for engaging at least one of the annular and axial slots to maintain the eddy current probe at a fixed distance from surfaces of the annular slot when the eddy current probe is caused to travel through the annular slot. The inspection further includes means for causing the eddy current probe to travel through the annular slot in a circumferential direction of the turbine wheel so as to enable the eddy current probe to electromagnetically inspect the annular slot and at least one of the axial slots. The method of this invention generally includes placing into the annular slot an eddy current probe configured as described above. Once in place, the eddy current probe is caused to travel through the annular slot in a circumferential direction of the turbine wheel to electromagnetically inspect the annular slot.

The eddy current probe can be individually inserted into the annular slot to perform an inspection on the immediate surfaces of the annular slot, or one of multiple eddy current probes interconnected together as a continuous unit that travels through the annular slot to perform inspections on surfaces of the annular slot. With any of the embodiments, it can be seen that the present invention is able to provide an inspection process for turbine wheels having dovetail slots that intersect an annular cooling slot, and in particular for inspecting the surfaces of the cooling slot. According to a preferred aspect of the invention, the eddy current probe is sized and configured to be placed in the cooling slot through one of the dovetail slots, such that the inspection process can be performed by removing the buckets from the dovetail slots to gain access to the cooling slot, without necessitating further disassembly of the wheel.

Other objects and advantages of this invention will be better appreciated from the following detailed description.

DETAILED DESCRIPTION OF THE INVENTION

Figure 1:
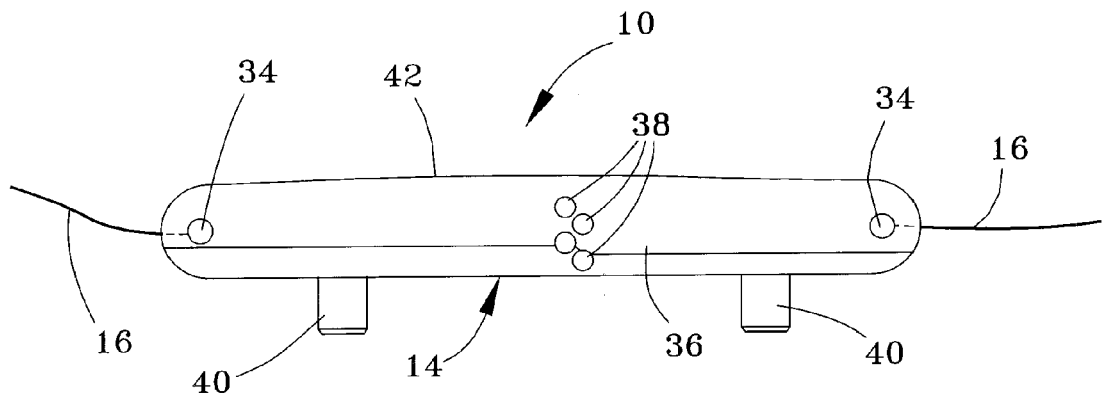
FIG. 1 is a perspective view of an eddy current probe assembly in accordance with a first embodiment of this invention.
Figure 2:
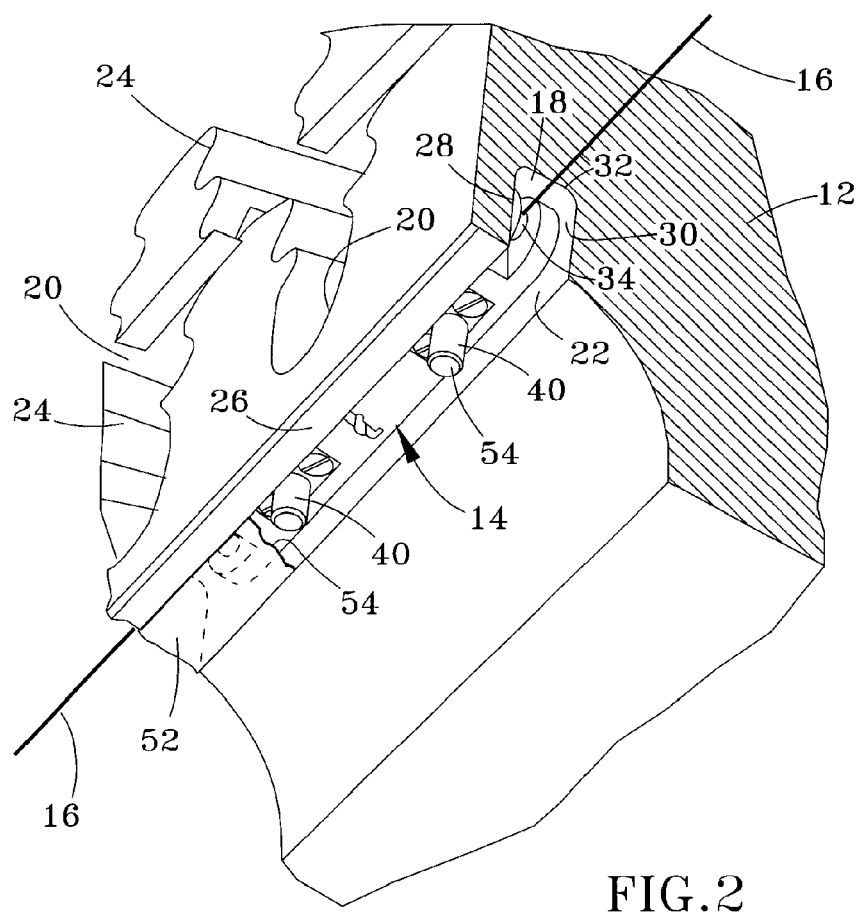
FIGS. 2 and 3 are two perspective views from different angles of the probe assembly of FIG. 1 placed in a cooling slot of a turbine wheel for inspection of dovetails slots within the vicinity of the cooling slot in accordance with the first embodiment of this invention.
Figure 3:
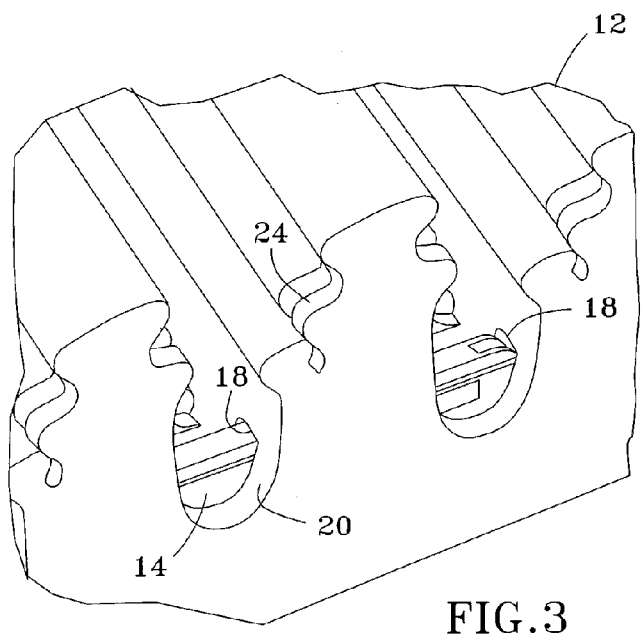

FIG. 1 depicts an eddy current probe assembly 10 configured for performing a nondestructive examination (NDE) of a turbine wheel 12 as depicted in FIGS. 2 and 3 in accordance with a first embodiment of the present invention. The probe assembly 10 comprises a probe 14 to which two flexible cables 16 are attached at opposite longitudinal ends of the probe 14. The cables 16 must be sufficiently strong to be used to pull the probe 14 through an annular cooling slot 18 formed in an axial face of the turbine wheel 12, as represented in FIGS. 2 and 3. For this purpose, each cable 16 may be a single strand of wire, braided wires, or an electrical cable, the latter of which would also serve to electrically connect the probe 14 to appropriate instrumentation (not shown), which typically includes an electrical (e.g., Wheatstone) bridge. The cooling slot 18 is radially inward from radially inward-extending dovetail slots 20 that are circumferentially spaced along the perimeter of the wheel 12, as is conventional for turbine wheels of industrial gas turbines. As is also conventional, the geometry of each dovetail slot 20 comprises contoured surfaces with facing lobes, and the plane of symmetry of each dovetail slot 20 is not parallel to the axis of the wheel 12, but is offset by some acute angle from the wheel axis. The particular configuration represented in the Figures is that of the General Electric 7FA stage 1 wheel, though other wheel configurations are within the scope of this invention. The dovetail slots 20 intersect the cooling slot 18 at their radially inward extremities, such that cooling flow through the cooling slot 18 conducts heat away from buckets (not shown) secured in the dovetail slots 20.

As is evident from FIG. 2, any tension applied to the cables 16 in the circumferential direction through the cooling slot 18 will produce a force component in a radially inward direction toward the axis of the wheel 12, forcing the probe 14 out of the slot 18 through its radially inboard-facing slot opening 22. Accordingly, the probe assembly 10 requires a structure capable of supporting the probe 14 within the cooling slot 18. As depicted in FIG. 2, such a structure may be in the form of a panel 52 (a limited portion of which is shown in FIG. 2) configured to at least close a sufficient portion of the slot opening 22 to support the probe 14 within the slot 18. In a preferred embodiment, the panel 52 has an annular shape that is sized to fit snugly against a lip 26 that defines one half of the slot opening 22 and an axially-outboard wall 28 of the cooling slot 18. A variety of materials could be used for the panel 52, such as a stainless steel about 0.005 to 0.010 inch (about 127 to 254 micrometers) in thickness.

As shown in FIGS. 1 and 2, the cables 16 can be attached to the ends of the probe 14 with pins 34 mounted between devises defined at the ends of the probe 14. In addition to pulling the probe 14 through the cooling slot, 18, the opposing tensions applied to the probe 14 through the cables 16 serve to stabilize and hold the probe 14 in place within the cooling slot 18. To promote stability, the probe 14 is preferably sized relative to the cooling slot 18 so that the side walls 28 and 30 of the cooling slot 18 maintain the orientation of the probe 14 within the slot 18, while the panel 52 positions the probe 14 relative to the radially-outward wall 32 of the slot 18. In this manner, the tension of the cables 16 and the close fit between the probe 14 and cooling slot 18 promote controlled motion of the probe 14 when it is moved with the cables 18 during scanning.

The body 36 of the probe 14 can be formed of a durable plastic or metal, preferred materials being those that will not scratch or mar the walls 28, 30, and 32 of the cooling slot 18. Suitable sizes for the probe 14 will depend in part on the cross-sectional dimensions and radius of curvature of the slot 18. For use with the General Electric 7FA stage 1 wheel, a suitable length for the probe 14 is about 1.1 cm in length. The probe body 36 contains cavities 38 that contain test coils (not shown) of any type suitable for use in eddy current scanning, such as ferrite-shielded probe coils available from Staveley NDT Technologies and having coil diameters of about 0.110 inch (about 2.8 mm). As noted above, electrical connection to the test coils can be made through one or both of the cables 16. In the configuration shown in FIG. 1, the test coils are arranged in an staggered two-dimensional array. The test coils can be operated in any suitable manner, such as being pulsed simultaneously or multiplexed to simulate movement in the circumferential direction through the cooling slot 18. By appropriately orienting the test coils within the probe body 36, the probe 14 can be used to scan all three walls 28, 30, and 32 of the cooling slot 18, as is evident from FIG. 3. The embodiment of FIGS. 1 through 4 preferably employs reference coils, which are preferably located within the probe 14 though it is foreseeable that reference coils could be located externally in a junction box (not shown).

Because the electrical output signal of an eddy current probe is maximized by maintaining contact between the probe and the surface being scanned (thereby minimizing lift-off noise), the probe 14 is preferably biased into contact with the outward wall 32 of the cooling slot 18. Another benefit of maintaining contact between the probe 14 and outward wall 32 is enhanced stability of the probe 14, which reduces probe wobble noise in the output signal of the probe 14. For maintaining contact, FIG. 1 depicts the probe 14 as having a pair of pins 40 that are biased outwardly from the probe body 36 with springs (not shown) or other suitable biasing means. The pins 40 are shown as facing the panel 52, such that sliding contact occurs between the pins 40 and a surface 54 the panel 52 facing the cooling slot 18. To minimize friction between the pins 40 and panel surface 54, the pins 40 may be formed of silicone or a composite containing graphite in a thermoset matrix, though a variety of other materials could be used as the pin material. The surface 42 of the probe body 36 opposite the pins 40 is urged into surface-to-surface contact with the outward wall 32 of the cooling slot 18. For this reason, the contact surface 42 preferably has a radius of curvature approximately equal to that of the slot outward wall 32.

Figure 4:
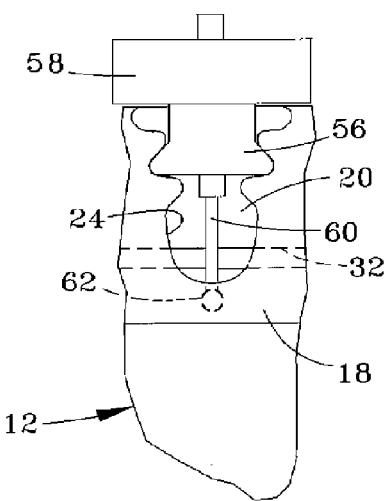
FIG. 4 is an axial view of the turbine wheel showing an apparatus for moving the probe of FIG. 1 through the cooling slot in accordance with the first embodiment of this invention.

With the embodiment of FIGS. 1 through 3, the cables 16 can be used to pull one or more probes 14 through the entire circumference of the cooling slot 18. For example, the probe 14 can be coupled to a drive motor (not shown) with the cables 16, which can be routed through two different dovetail slots 20 with support and mounting blocks 56 and 58 as depicted in FIG. 4. The mounting block 58 supports a shaft 60 that extends through the support block 56 and terminates with a pulley 62, whose position within the cooling slot 18 can be adjusted with the shaft 60 to obtain to the desired radial position of probe 14. One probe cable 16 would be used to pull the probe 14, while the other is used to maintain tension in the cables 16 through a second motor against which the drive motor works. Using an electronic control system common in motion control systems, e.g., available from the Compumotor Division of Parker Hannifin, Inc., the tension in the cables 16 and the speed of the probe 14 through the cooling slot 18 can be accurately controlled. By monitoring the positions of the cables 16, the location of the probe 14 within the cooling slot 18 can be measured, recorded and monitored so that any cracks detected can be related to a position in the cooling slot 18. For this purpose, a computer system (not shown) can be used to remotely control the motion of the probe 14 and record the position and eddy current signals of the probe 14. A preferred system includes analysis software for control, operation, and analysis of the eddy current data, along with suitable displays. The probe operation may be singly or multiplexed for array operation, or in a subset of these configurations. Multichannel parallel operation is also possible. It is also foreseeable that a single probe 14 or multiple interconnected probes 14 could be configured for fully remote operation by incorporating a battery pack, motorized friction drive, eddy current test coils, eddy current reference coils, instrumentation and on-board controls, and a wireless interface for communication with a remote control unit.

Figure 5:
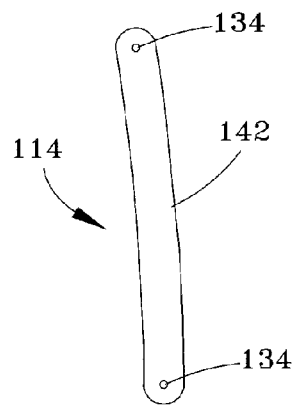
FIGS. 5 and 6 are side views of an eddy current probe in accordance with a second embodiment of this invention.
Figure 6:
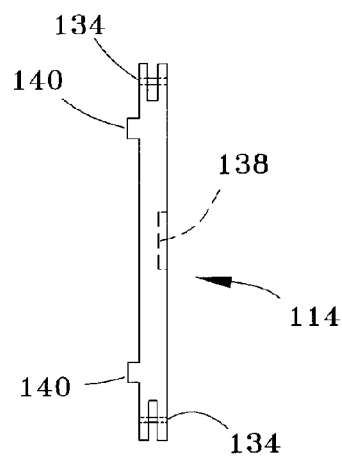
Figure 7:
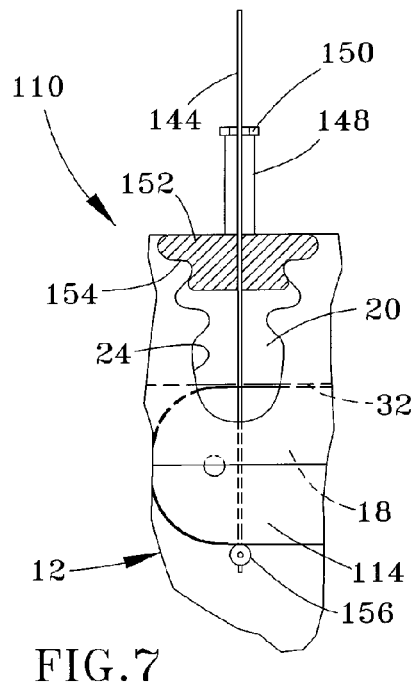
FIG. 7 is an axial view of a portion of a turbine wheel showing the probe of FIGS. 5 and 6 placed in a cooling slot of the turbine wheel in accordance with the second embodiment of this invention.

In a second embodiment of the invention depicted in FIGS. 5, 6, and 7, a probe assembly 110 is provided that does not require the panel 52 and omits the cables 16 of the first embodiment, while making possible an inspection process that can be remotely controlled. Instead of cables, the probe assembly 110 makes use of multiple pivotally interconnected probe segments 114 as shown in FIG. 7, one of which is shown in FIGS. 5 and 6. Similar to the probe 14 of FIGS. 1 through 3, the outer surface 142 of each segment 114 is curved to match the curvature of the cooling slot 18. Also similar, the probe segments 114 are equipped with test coils (not shown) contained in a recess 138 in a sidewall of the segment 114. As with the embodiment of FIGS. 1 through 4, the second embodiment preferably employs reference coils that may be located within the probe 114 or located externally. A pair of pads 140 project from the opposite sidewall of each segment 114 to assist with axial alignment of the segments 114 within the cooling slot 18.

The length, width, and shape of each probe segment 114 is selected to enable the segments 114 to be placed in the cooling slot 18 through the bucket dovetail slot 20. Adjacent probe segments 114 can be connected end-to-end using pins or clips 134. Any number of probe segments 114 can be connected together in this manner. For example, a sufficient number of probe segments 114 can be assembled to encompass the entire 360 degrees of the cooling slot 18. In a probe assembly 110 made up of multiple probe segments 114, test coils can be omitted from some of the segments 114, such that these inactive segments 114 serve only to promote the mechanical stability of the assembly 110. However, it is within the scope of the invention that all segments 114 can be equipped with test coils and thereby operate as active eddy current probes. The interconnected segments 114 can be inserted into the cooling slot 18 through one of the dovetail slots 20. The first segment 114 can be grasped with a standard three-prong flexible gripper inserted through an adjacent dovetail slot 20 to pull the probe assembly 110 through the cooling slot 18. A flexible cable (not shown) may also be attached to the probe assembly 10 to assist with positioning the assembly 110 in the cooling slot 18. The cable may also serve as the conduit for electrical connection for the assembly 110 to appropriate instrumentation (not shown).

To maintain each probe segment 114 in contact with the outward wall 32 of the cooling slot 18, a radially-outward mechanical force is applied to the probe segments 114 with a support shaft 144. A bearing support 156 is shown mounted at the lower end of the shaft 144 and oriented to extend under that portion of the probe segment 114 exposed within the dovetail slot 20. The space between the pads 140 of the probe segment 114 provides a gap through which the shaft 144 is able to pass to the radially-inward surface of the segment 114. The shaft 144 is held in a radially-outward direction through the combination of a spring 148 and nut 150 threaded onto the shaft 144. The spring 148 is biased against a support block 152 whose shaped profile 154 is complementary to at least a portion of the dovetail slot geometry 24, such that the support block 152 can be axially inserted into the dovetail slot 20 similar to when installing a bucket in the dovetail slot 20. The spring-loaded shaft 144 and support block 152 ensure that the probe segment 114 remains in contact with the outward wall 32 of the slot 18, while the support 156 supports the probe segment 114 in a manner that allows the segment 114 to move in the circumferential direction of the slot 18. By spring loading the shaft 144, the operator's hands are free to scan the probe assembly 110 through the cooling slot 18 while operating the instrumentation for the eddy current probe assembly 110.

As evident from the above, the embodiment of FIGS. 5 through 7 can be operated to scan a region of the cooling slot 18 in the immediate vicinity of the dovetail slot 20 from which the probe assembly 110 is supported. Instead of a bearing affixed to the shaft 144, bearings could be provided on the probe segment 114 to reduce sliding friction between the probe segment 114, support 156, and surface being examined. Motorized remote control of the scanning operation can be achieved using essentially the same approach as that described for the embodiment of FIGS. 1 through 4.

As an alternative to the spring-loaded shaft 144 of the preceding embodiment, one or more of the segments 114 may be equipped with a spring or other biasing element (not shown) to apply a circumferential bias, so that a multi-segmented probe assembly 110 can be assembled to form a complete ring in which the circumferential bias generated by the one or more segments 114 causes the entire assembly 110 to radially expand outward into contact with the outward surface 32 of the cooling slot 18. As an alternative, a linear actuator could be used in place of one or more of the segments 114. Because the shaft 144 extends beneath the probe segment 114 through a gap created between the segment 114 and one of the walls of the cooling slot 18 that by the pads 140 on the segment 114 (FIG. 7), the pads 140 will prevent full circumferential movement of a multi-segmented probe assembly 110 assembled as a complete ring. Therefore, in order to achieve greater movement, the pads 140 would be removed as needed during the scanning of the cooling slot 18, or entirely eliminated. Another alternative is to replace the pads with a turnstile sprocket (not shown) that provides support and can allow the shaft 144 to push past the sprocket.

Figure 9:
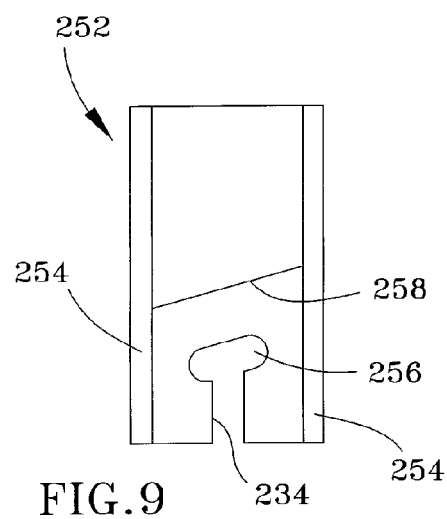
FIG. 9 is a plan view of a support block of the probe assembly of FIG. 8.
Figure 8:
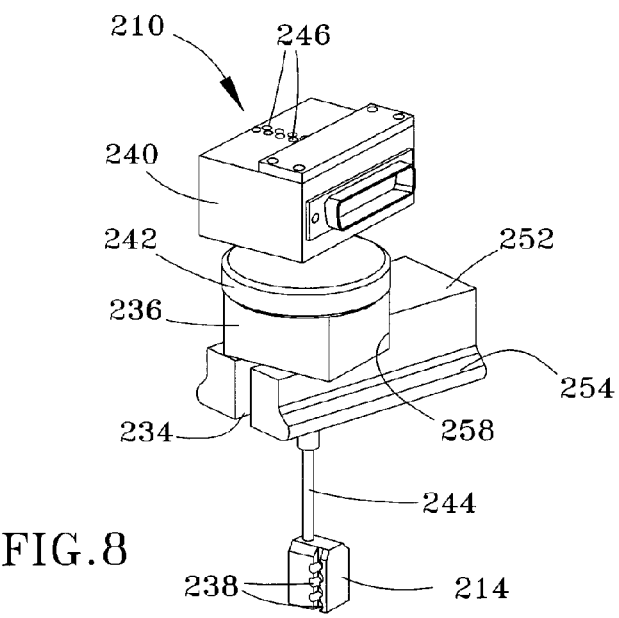
FIG. 8 is a perspective view of an eddy current probe assembly in accordance with a third embodiment of this invention.
Figure 10:
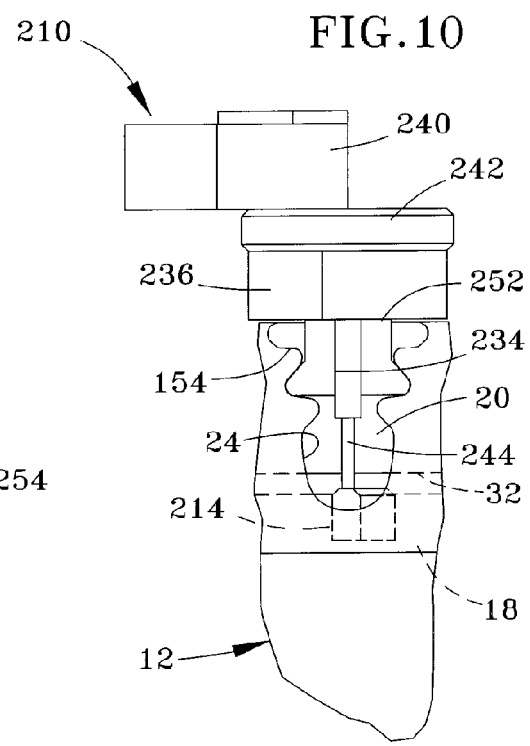
FIG. 10 is an axial view of a portion of a turbine wheel showing the probe assembly of FIG. 8 placed in a cooling slot of the turbine wheel in accordance with the third embodiment of this invention.

FIGS. 8, 9, and 10 depict a simpler probe assembly 210 that permits the examination of the cooling slot 18 and the immediately surrounding surface regions of a dovetail slot 20 in which the probe assembly 210 is placed. The probe assembly 210 includes a probe 214 mounted to one end of a shaft 244. Test coils are housed within cavities 238 formed in the probe 214 and wired to a connector block 240 mounted to the opposite end of the shaft 244. An adjustment ring 242 is threaded onto the shaft 244 and enables the position of the probe 214 to be radially adjusted relative to the dovetail slot 20, in which the assembly 210 is held by a support block 252. Similar to the support block 152 of the second embodiment, the support block 252 has a profile 254 that is complementary to a portion of the dovetail slot geometry 24, such that the support block 252 can be axially inserted into the dovetail slot 20. As more readily seen from FIG. 9, which shows the support block 252 separate from the remainder of the probe assembly 210, the support block 252 is assembled onto the shaft 244 by sliding the shaft 244 through a slot 234 defined at one end of the support block 252. The slot 234 has a generally T-shaped profile when viewed in a direction parallel to the shaft 244, such that once placed in the slot 234 the shaft 244 is able to travel in a transverse camming portion 256 of the slot 234. As evident from FIG. 10, the support block 252 anchors the entire probe assembly 210 and establishes the positional reference when controlling the position of the probe 214 relative to the cooling and dovetail slots 18 and 20.

A slide block 236 is mounted between the adjustment ring 242 and support block 252, and is secured to the support block 252 with the ring 242. The slide block 236 cams against a shoulder 258 on the upper surface of the support block 252. The shoulder 258 is disposed at the same angle to the axial direction as the camming portion 256 of the slot 234, such that sliding movement of the slide block 236 and the shaft 244 occur in the same direction. This movement of the slide block 236 and shaft 244 allows limited bidirectional scanning of the probe 214 through the cooling slot 18. The angular offset of the camming portion 256 and shoulder 258 is intended to accommodate the angle of the dovetail slots 20 relative to the axis of the wheel 12. In the General Electric 7FA stage 1 wheel, this angle is about 74.5 degrees to the wheel axis.

From FIGS. 8 and 10, it can be seen that the uppermost cavity 238 housing a test coil is disposed at an angle of about forty-five degrees relative to the other cavities 238, enabling its test coil to inspect the cooling slot fillet closest to the radial plane of the wheel 12. The connector block 240 is equipped with a staggered array of cavities 246 in which reference coils can be placed for the eddy current system. The reference coils are preferably operated as an array of eddy current sensors, as is conventional for a differential probe system. Another option is to place the reference coils near the instrument end of the electrical cable bundle (not shown) of the probe assembly 210, which has the advantage of reducing the size of the cable bundle at its point of attachment to the probe assembly 210. Once the reference coils are mounted in their desired location, the performance of the array of reference coils can be adjusted by covering the coils with a sheet formed of the same alloy from which the wheel 12 is formed. Ideally, the reference coils are recessed into their cavities 258 so as to be spaced apart from the sheet a distance equal to the mean gap that will exist between the test coils of the probe 214 and the surfaced 28, 30, and 32 they are scanning.

While the invention has been described in terms of particular embodiments, it is apparent that other forms could be adopted by one skilled in the art. For example, the physical configurations of the probe assemblies 10, 110, and 210 and of the wheel 12 being inspected could differ from that shown. Therefore, the scope of the invention is to be limited only by the following claims.

What is claimed is:

1. A method of inspecting a turbine wheel having axial slots along a perimeter thereof and an annular slot that intersects the axial slots, the axial slots having a geometry configured for mating with and securing airfoil members to the perimeter of the wheel, the method comprising the steps of:
    placing an eddy current probe of a probe assembly into the annular slot, the probe assembly comprising a mounting member to which the eddy current probe is mounted and means for engaging at least one of the annular and axial slots to maintain the eddy current probe at a fixed distance from surfaces of the annular slot when the eddy current probe is caused to travel through the annular slot; and
    causing the eddy current probe to travel through the annular slot in a circumferential direction of the turbine wheel and electromagnetically inspect the annular slot and at least one of the axial slots for cracks in the surfaces thereof.

2. The method according to claim 1, wherein the eddy current probe comprises a plurality of test coils that generate electromagnetic fields for simultaneously inspecting multiple surfaces of the annular and axial the electromagnetic field of at least one of the test coils being generated at an angle of about forty-five degrees to the electromagnetic field generated by a second of the test coils.

3. The method according to claim 1, wherein the eddy current probe is caused to travel through the annular slot by first and second flexible cables extending through the annular slot and attached to oppositely-disposed ends of the eddy current probe, and the causing step comprises pulling the eddy current probe through the annular slot with the first flexible cable while keeping the second flexible cable taut.

4. The method according to claim 1, wherein the annular slot has an annular opening and the mounting member comprises an annular member, the method further comprising the step of mounting the annular member to the turbine wheel to close the annular opening with a surface thereof.

5. The method according to claim 4, further comprising the step of biasing the eddy current probe away from the annular member and toward an oppositely-disposed surface of the annular slot.

6. The method according to claim 1, wherein the eddy current probe is one of a plurality of eddy current probes interconnected, and each of the plurality of eddy current probes is caused to travel through the annular slot during the causing step.

7. The method according to claim 6, wherein the plurality of eddy current probes are interconnected to define a continuous circular array of eddy current probes that extends the entire circumferential length of the annular slot.

8. The method according to claim 7, wherein the engaging means of the mounting member is a profile of the mounting member configured to engage the geometry of any one of the axial slots, the placing step comprises axially inserting the mounting member into one of the axial slots to engage the profile of the mounting member with the geometry of the one axial slot, the method further comprising biasing the eddy current probe toward the mounting member.

9. The method according to claim 1, wherein the engaging means of the mounting member is a profile of the mounting member configured to engage the geometry of any one of the axial slots, the placing step comprises axially inserting the mounting member into one of the axial slots to engage the profile of the mounting member with the geometry of the one axial slot, the method further comprising biasing the eddy current probe toward the mounting member.

10. The method according to claim 1, wherein the eddy current probe is placed into the annular slot through one of the axial slots.

11. An inspection system for a turbine wheel having axial slots along a perimeter thereof and an annular slot that intersects the axial slots, the axial slots having a geometry configured for mating with and securing airfoil members to the perimeter of the wheel, the inspection system comprising:
    a probe assembly comprising an eddy current probe and a mounting member, the eddy current probe being sized and configured to be received in the annular slot, the mounting member having means for engaging at least one of the annular and axial slots to maintain the eddy current probe at a fixed distance from surfaces of the annular slot when the eddy current probe is caused to travel through the annular slot; and means for causing the eddy current probe to travel through the annular slot in a circumferential direction of the turbine wheel so as to enable the eddy current probe to electromagnetically inspect the annular slot and at least one of the axial slots for cracks in the surfaces thereof.

12. The inspection system according to claim 11, wherein the eddy current probe comprises a plurality of test coils that generate electromagnetic fields for simultaneously inspecting multiple surfaces of the annular and axial slots, at least one of the test coils being oriented to generate an electromagnetic field at an angle of about forty-five degrees to the electromagnetic field of a second of the test coils.

13. The inspection system according to claim 11, wherein the causing means comprises first and second flexible cables extending through the annular slot and attached to oppositely-disposed ends of the eddy current probe.

14. The inspection system according to claim 11, wherein the annular slot has an annular opening and the mounting member is an annular member that is mounted to the turbine wheel to close the annular opening with a surface thereof.

15. The inspection system according to claim 14, wherein the engaging means further comprises means for biasing the eddy current probe away from the annular member and toward an oppositely-disposed surface of the annular slot.

16. The inspection system according to claim 11, wherein the eddy current probe is one of a plurality of eddy current probes interconnected to travel together through the annular slot.

17. The inspection system according to claim 16, wherein the plurality of eddy current probes are interconnected to define a continuous circular array of eddy current probes that extends the entire circumferential length of the annular slot.

18. The inspection system according to claim 17, wherein the engaging means of the mounting member is a profile of the mounting member configured to engage the geometry of one of the axial slots, the engaging means further comprising means for biasing the eddy current probe toward the mounting member.

19. The inspection system according to claim 11, wherein the engaging means of the mounting member is a profile of the mounting member configured to engage the geometry of one of the axial slots, the engaging means further comprising means for biasing the eddy current probe toward the mounting member.

20. The inspection system according to claim 11, wherein the eddy current probe is received in the annular slot.

* * * * *